US009145515B2

(12) United States Patent
Sotzing

(10) Patent No.: US 9,145,515 B2
(45) Date of Patent: Sep. 29, 2015

(54) SCREENING PROCESSES, CONDUCTING POLYMERS, AND ELECTROCHROMIC DEVICES BASED ON DIFFUSIONAL GRADIENTS

(71) Applicant: Gregory A. Sotzing, Storrs, CT (US)

(72) Inventor: Gregory A. Sotzing, Storrs, CT (US)

(73) Assignee: THE UNIVERSITY OF CONNECTICUT, Farmington, CT (US)

( * ) Notice: Subject to any disclaimer, the term of this patent is extended or adjusted under 35 U.S.C. 154(b) by 35 days.

(21) Appl. No.: 13/948,712

(22) Filed: Jul. 23, 2013

(65) Prior Publication Data

US 2014/0024792 A1    Jan. 23, 2014

Related U.S. Application Data

(60) Provisional application No. 61/674,482, filed on Jul. 23, 2012, provisional application No. 61/711,248, filed on Oct. 9, 2012.

(51) Int. Cl.
*C09K 9/02* (2006.01)
*G01N 33/44* (2006.01)

(52) U.S. Cl.
CPC .............. *C09K 9/02* (2013.01); *G01N 33/442* (2013.01); *C08G 2261/1424* (2013.01); *C08G 2261/3223* (2013.01); *C08G 2261/44* (2013.01); *C08G 2261/54* (2013.01); *C09K 2211/1458* (2013.01); *C09K 2211/1491* (2013.01)

(58) Field of Classification Search
CPC ......................................... C09K 9/02
USPC .............................. 526/256; 506/12; 528/377
See application file for complete search history.

(56) References Cited

U.S. PATENT DOCUMENTS 7,586,663 B1    9/2009   Radmard et al.
7,626,748 B2    12/2009  Radmard et al.

*Primary Examiner* — Duc Truong
(74) *Attorney, Agent, or Firm* — Cantor Colburn LLP

(57) ABSTRACT

Disclosed herein is a high throughput screening method which allows for the efficient and economical color screening of electrochromic copolymers with different monomer feed ratios. The process uses the diffusion behavior of the starting monomers at different concentrations to obtain diffusion coefficients, which can be used to quantify the monomer feed ratio for a given copolymer. Also disclosed herein are devices used in the process, conjugated copolymers obtained by using the method where the copolymers exhibit a certain property based on the monomer feed ratio, and devices made from the conjugated copolymers.

13 Claims, 4 Drawing Sheets
(4 of 4 Drawing Sheet(s) Filed in Color)

SCREENING PROCESSES, CONDUCTING POLYMERS, AND ELECTROCHROMIC DEVICES BASED ON DIFFUSIONAL GRADIENTS

CROSS-REFERENCE TO RELATED APPLICATIONS

This application claims the benefit of U.S. Provisional Application Ser. No. 61/674,482, filed Jul. 23, 2012 and U.S. Provisional Application Ser. No. 61/711,248 filed Oct. 9, 2012, both of which are incorporated herein by reference in their entirety.

BACKGROUND

Conducting polymers exhibit electrochromism, the ability to reversibly switch colors when external electronic biases are applied. Owing to their flexibility, low cost and high coloration efficiency, conducting polymers have desirable properties not found in other known electrochromic materials, such as inorganic oxides and small organic molecules. The extended π conjugation along the conducting polymer backbone renders optical absorption which often falls in the visible region. The energy gap between the HOMO and LUMO changes with the external bias, and results in absorption shift and visible color change.

The achievable color is an intrinsic property of a specific conducting polymer material, and is applicable to color-related electrochromic applications. For example, poly(3,4-ethylenedioxythiophene) (PEDOT), shows a signature blue color which is darker in the neutral state and lighter in the oxidized state. Some conducting polymers shows polychromism, which means they may have intermediate color states. By tuning the polymer chemical structure, the electronic character of the π system can be adjusted to give different colors. For example, poly(dimethyl-3,4-propylenedioxythiophene) (PPropOT-Me$_2$) switches between purple and light sky-blue.

Copolymerization of two different monomers is one way to obtain new colors without additional chemical modification. Copolymers with precise composition have been made by chemical polymerization in order to achieve the desired color spectrum. Additionally, copolymerization has been carried out by electrochemistry, however, the resulting copolymers did not necessarily have the same composition as the feeding component ratio. In either chemical or electrochemical polymerization, a laborious process is usually involved: products with different combination and ratios of the monomer components have to be synthesized and characterized in separate batches. In addition to the time consuming process, a large amount of electrolyte solvent, salt and leftover monomers generated from each batch raise environmental concerns.

Electrochromic devices are traditionally fabricated by first depositing electrochromic films on indium-doped tin oxide (ITO) substrates from a monomer solution, and then assembling the film into a device by sandwiching a UV-curable polymer electrolyte between the ITO with electrochromic film and another piece of bare ITO electrode. The polymer electrolyte crosslinks upon UV exposure, changes from liquid to a solid-state transparent gel which holds the two ITO pieces together. This method is not efficient because the film quality is greatly affected by the cleanliness of the substrates, the monomer solution, and the method generates a large amount of waste.

Recently, an in situ electrochromic device (ECD) assembly approach has been developed. In this method, electrochromic monomer is mixed with electrolyte before crosslinking, and polymerization of the electrochromic monomer occurs after the device assembly in the solid-state. This method not only significantly increases the success rate of the device fabrication, but also renders a solid gel matrix inside the device before the polymerization of the electrochromic monomers.

There remains a need in the art for methods to rapidly and efficiently determine the color of electrochromic copolymers to significantly accelerate the color selection process.

BRIEF SUMMARY

In one embodiment, a method for screening comprises providing a screening device comprising at least two electrodes and a polymer electrolyte matrix disposed between the at least two electrodes, wherein the polymer electrolyte matrix comprises a plurality of reservoirs; providing an electroactive monomer composition in the plurality of reservoirs, wherein the electroactive monomer composition comprises an electroactive monomer of a known concentration, a monomer composition solvent, and optionally a monomer composition salt, wherein each reservoir comprises a single electroactive monomer composition; allowing the electroactive monomer of the electroactive monomer composition to diffuse through the polymer electrolyte matrix for a period of time; polymerizing the electroactive monomer to form a composite of polymer electrolyte matrix and a conjugated polymer, or a composite of polymer electrolyte matrix and a conjugated copolymer where two or more different electroactive monomers have diffused into the same area of the polymer electrolyte matrix; determining the diffusion behavior of the monomer in the monomer compositions; obtaining a property of the conjugated polymer or conjugated copolymer; and correlating the property of the conjugated copolymers with monomer feed ratios.

In another embodiment, a method of forming an electrochromic device comprises using an electrochromic monomer mixture having a feed ratio that provides a select color, wherein the feed ratio is determined from a screening method.

In another embodiment, a conjugated copolymer having a select color is obtained by using the screening method.

In another embodiment, a conjugated copolymer comprises units of a blue monomer and units of a yellow monomer, wherein the conjugated copolymer exhibits a red color in its neutral state.

BRIEF DESCRIPTION OF THE DRAWINGS

The patent or application file contains at least one drawing executed in color. Copies of this patent or patent application publication with color drawings will be provided by the Office upon receipt and payment of the necessary fee. The components in the drawings are not necessarily to scale, emphasis instead being placed upon clearly illustrating the principles of the embodiments described herein.

FIG. 1A is a schematic illustration of a monomer screening device with a rectangular-shaped reservoir for monomer solution in the center; (B) the circled region illustrates the diffusion of the monomer, EDOT, which is colorless but is marked with shading in the Figure for clarity; (C) the diffusion radius can be observed by the color of the polymerized EDOT in the reduced (C) and oxidized (D) states.

FIG. 4A is a schematic of a high throughput color selection device setup and FIG. 4B shows the neutral state of the copolymer device of 50% EDOT and 50% bithiophene diffusion system.

DETAILED DESCRIPTION

Figures 1A, 1B, 1C, 1D:
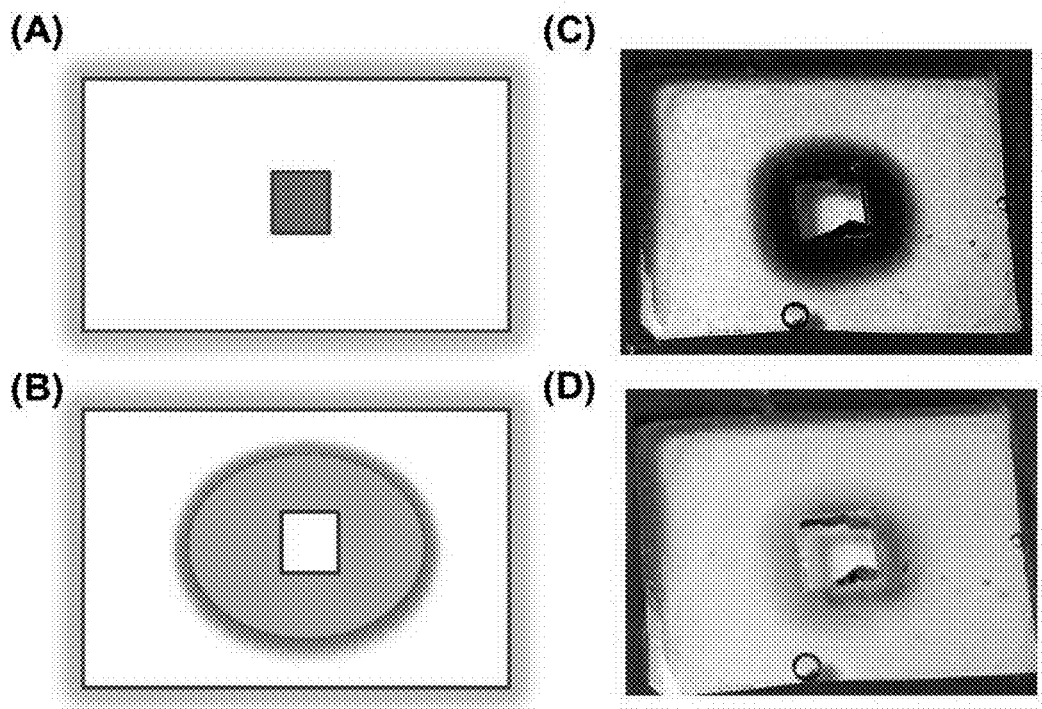
FIGS. 1A, 1B, 1C, and 1D.

Disclosed herein is a high throughput method for color selection for electrochromic copolymerization and display applications using the in situ electrochromic device (ECD) assembly approach. Also disclosed herein are copolymers and a method of making a copolymer having a select color based on the high throughput method. The color selection process employs the diffusion behavior of electrochromic monomers in a polymer electrolyte matrix and subsequent copolymerization of the monomer mixtures formed with different feeding ratios. Diffusion behavior of different monomers in a polymer electrolyte matrix was studied as diffusion results in the formation of a concentration gradient. Diffusion coefficient and concentration distribution were calculated for monomers with various initial concentrations. The diffusion coefficient was found to be related to the initial concentration and the size of the monomers. When more than one monomer is loaded in the polymer electrolyte matrix the diffusion results in a concentration gradient and different mix ratios of the monomers. From the mixtures, polymerization of the monomers results in copolymers with various compositions based on the monomer feed ratios. Copolymers with various compositions can be obtained and characterized in a single test.

As a color screening method the described process is able to measure color coordinates of copolymers with different monomer feed ratios in a single test, which is very efficient and material-economical. The complete color spectrum could be achieved in a single run. The method can also be used to predict the composition of monomers given a color. The high throughput color screening approach can accelerate the color selection process for electrochromic device and display applications. In addition, based on the monomer ratio, copolymers of select, unexpected colors can be achieved. For example, disclosed herein is a red conjugated copolymer, which is a primary color obtained from a certain feed ratio of a blue monomer and a yellow monomer. "Blue monomer" means a homopolymer prepared from the monomer provides a blue color in its neutral state when perceived by the human eye. Likewise, a "yellow monomer" means a homopolymer prepared from the monomer provides a yellow color in its neutral state when perceived by the human eye. According to the subtractive color mixing theory, a copolymer prepared from a blue monomer and a yellow monomer would be expected to provide a green color. Instead, the copolymer provided an unexpected red color.

The color screening process involves color matching between the copolymer colors and monomer feeding ratios. To achieve this, an in situ screening device is employed. The in situ screening device comprises, at least two electrodes, a potential source in electrical connection with the at least two electrodes, and a polymer electrolyte matrix, where the polymer electrolyte matrix comprises a plurality of reservoirs.

The diffusion behavior of electroactive monomers is determined using the in situ screening device. The process involves first investigating the diffusion behavior of individual electroactive monomers in a polymer electrolyte matrix before the color matching process. The diffusion behavior includes determining diffusion speed, concentration gradient, and the like using various known concentrations of monomer composition. The diffusion coefficients for the electroactive monomers are obtained in order to quantify the feed ratio. To quantitatively characterize the diffusion behavior of different electroactive monomers, monomer compositions of various concentrations containing a single electroactive monomer, a monomer composition solvent, and a monomer composition salt are prepared. The monomer compositions are added to the reservoirs of the screening device, one single monomer composition per reservoir. The electroactive monomer in each reservoir is allowed to diffuse through the surrounding polymer electrolyte matrix for a predetermined amount of time (e.g. any time point up to 24 hours). As it is present in the polymer electrolyte matrix, the diffused monomer composition is disposed between the at least two electrodes of the screening device. The electroactive monomer is then polymerized, for example by applying voltage to the device, to form a composite comprising a conjugated polymer and polymer electrolyte matrix composite. As used herein, a conjugated polymer is synonymous to an electrochromic polymer, an electroactive polymer, or a conducting polymer.

The diffusion coefficient D of each electroactive monomer composition is calculated according to the following equation where x is the distance the electroactive monomer travelled from the reservoir and t is the time of the diffusion.

$$x = \sqrt{2Dt} \qquad \text{Equation 1}$$

The diffusion coefficient was found to be inversely proportional to electroactive monomer size and is concentration dependent. It has also been determined that the diffusion behavior of a certain electroactive monomer is not affected by the presence of other electroactive monomer species present in the polymer electrolyte matrix. The conjugated polymer can be switched to its colored state for ease in determining the distance the electroactive monomer travelled through the matrix.

For each monomer composition, the saturation point, the point where diffusion is so slow that it is negligible in the time scale of the study; and the saturation distance, the farthest distance the electroactive monomer travelled at saturation point, are determined. Equipped with the diffusion behavior of the individual monomer compositions, a diffusion copolymer study can be performed where the electroactive monomers from two adjacent reservoirs are allowed to diffuse and mix at various concentrations (see FIGS. 4A and 4B). Saturation distance of a electroactive monomer is useful for color screening, because electroactive monomers with similar saturation distance will allow the maximum blending of the two using the diffusion copolymer approach. In addition, an appropriate distance between two reservoirs, each containing a different monomer composition, is determined by the saturation distance of two monomers. At the saturation point, the electroactive monomers are polymerized and copolymers are formed where the two electroactive monomers were mixed (See FIGS. 4A and 4B). The feeding ratio of the copolymerization depends on the monomer concentration distribution at the saturation point. The feeding concentration can be calculated by Equation 2, where y is the distance of the point of interest from the reservoir, D is the diffusion coefficient, $t_{sp}$ is the time needed to reach saturation point, c is the concentration at distance y, $c_2$ is the initial concentration, (i.e., the concentration of the monomer composition in the reservoir), and erfc is a Guassian function called "error function".

$$c = c_2 * \text{erfc}*(y/2\sqrt{Dt_{sp}})$$  Equation 2

Next, the relation between the electroactive monomer feeding ratios and copolymer composition is established by determining the colors of the copolymer using CIELuv color coordinates (u', v') for various points along the diffusion path between the two reservoirs at set distance intervals. Thus, as a color screening method, one is able to measure color coordinates of copolymers with different electroactive monomer feed ratios in a single test. Furthermore, using the system, it is also possible to predict the composition of electroactive monomers given a color.

It has been found that the color coordinates of the copolymers formed in the screening device matches with those of unmodified in situ prepared devices with similar compositions.

The polymer electrolyte matrix for use in the screening device includes those polymer electrolyte compositions known for use in electrochromic devices. The electrolyte composition may include metal salts, organic salts (e.g., ionic liquids), inorganic salts, and the like, and a combination thereof.

The plurality of reservoirs (wells) in the polymer electrolyte matrix allows for the feeding of different electroactive monomer compositions. Different electroactive monomers exhibit different diffusion behaviors in the polymer electrolyte matrix such as diffusion speed, concentration gradient, and the like. The polymer electrolyte matrix can be a crosslinked gel electrolyte composition. In one embodiment, the polymer electrolyte matrix includes UV cured gel electrolyte such as a crosslinked poly(ethylene glycol) matrix containing lithium trifluoromethanesulfonate as the charge carrier and is plasticized by propylene carbonate. Propylene carbonate acts as a solvent inside the polymer electrolyte matrix and is the diffusion medium. The crosslinked gel electrolyte composition can be prepared by crosslinking a gel electrolyte precursor mixture, wherein the mixture comprises a gel electrolyte precursor, electrolyte salt, and an optional gel electrolyte precursor solvent.

In one embodiment the electrolyte composition is a gel electrolyte. The gel electrolyte layer can be formed by coating a gel electrolyte precursor mixture comprising a gel electrolyte precursor. The gel electrolyte precursor can be monomeric or polymeric. In particular, the gel precursor is a crosslinkable polymer. The crosslinkable polymer can comprise polymerizable end groups, polymerizable side-chain groups, or a combination thereof attached to a polymer backbone. Exemplary polymer backbones include polyamides, polyimides, polycarbonates, polyesters, polyethers, polymethacrylates, polyacrylates, polysilanes, polysiloxanes, polyvinylacetates, polymethacrylonitriles, polyacrylonitriles, polyvinylphenols, polyvinylalcohols, polyvinylidenehalides, and co-polymers and combinations thereof. More specifically, the gel precursor is a cross-linkable polyether. Exemplary polyethers include poly(alkylene ethers) and poly(alkylene glycol)s comprising ethyleneoxy, propyleneoxy, and butyleneoxy repeating units. Hydroxyl end groups of poly(alkylene glycols) can be capped with polymerizable vinyl groups including (meth)acrylate and styryl vinyl groups to form a crosslinkable polyether. In particular, the crosslinkable polymer is selected from the group consisting of poly(ethylene glycol)diacrylate (PEG-DA), poly(propylene glycol)diacrylate (PPG-DA), poly(butylene glycol)diacrylate (PBG-DA), poly(ethylene oxide) (PEO), poly(propylene oxide) (PPO), poly(butylene oxide) (PBO), and combinations thereof. The crosslinkable polymer can also be a copolymer or a block copolymer comprising ethyleneoxy, propylenoxy, or butyleneoxy repeating units. In one embodiment, the gel precursor is PEO and is crosslinked thermally. In one embodiment, the gel precursor is PEO and is crosslinked using UV radiation. In a specific embodiment, the gel precursor is crosslinkable polymer comprising a mixture of PEG-DA and PEO, wherein the PEO:PEG-DA weight ratio is from 95:5 to 5:95, more particularly 90:10 to 10:90, and even more particularly 60:40 to 40:60 or 50:50.

The electrolyte composition can comprise an alkali metal ion of Li, Na, or K. Exemplary electrolytes, where M represents an alkali metal ion, include $MClO_4$, $MPF_6$, $MBF_4$, $MAsF_6$, $MSbF_6$, $MCF_3SO_3$, $MCF_3CO_2$, $M_2C_2F_4(SO_3)_2$, $MN(CF_3SO_2)_2$, $MN(C_2F_5SO_2)_2$, $MC(CF_3SO_2)_3$, $MC_nF_{2n+1}SO_3$ ($2 \leq n \leq 3$), $MN(RfOSO_2)_2$ (wherein Rf is a fluoroalkyl group), MOH, or combinations of the foregoing electrolytes. In particular, the electrolyte composition comprises a lithium salt. More particularly, the lithium salt is lithium trifluoromethanesulfonate. Other suitable salts include tetra-n-butylammonium tetrafluoroborate ($TBABF_4$); tetra-n-butylammonium hexafluorophosphate ($TBAPF_6$); and combinations thereof. When a gel electrolyte is used, the concentration of the electrolyte salt may be about 0.01 to about 30% by weight of the gel electrolyte precursor, specifically about 5 to about 20% by weight, and yet more specifically about 10 to about 15% by weight of the gel electrolyte precursor.

The gel electrolyte precursor mixture can also comprise a solvent or plasticizer to enhance the ionic conductivity of the electrolyte. These may be high boiling organic liquids such as carbonates, their blends or other materials like dimethylformamide (DMF). In particular the solvent can be a carbonate, for example alkylene and alkylyne carbonates such as dimethyl carbonate, ethylmethyl carbonate, methylpropyl carbonate, methylbutyl carbonate, methylpentyl carbonate, diethyl carbonate, ethylpropyl carbonate, ethylbutyl carbonate, dipropyl carbonate, propylene carbonate, ethylene carbonate, propylyne carbonate, and combinations thereof. The amount of solvent and/or plasticizer added to the gel electrolyte precursor mixture can range from about 0 to about 50% by weight of the gel electrolyte precursor mixture, specifically about 10 to about 40% by weight, and more specifically about 20 to about 30% by weight of the gel electrolyte precursor mixture.

The gel electrolyte precursor mixture can further comprise other additives such as photochemical sensitizers, free radical initiators, and diluent polymers, providing the desired properties of the electrochromic device are not significantly adversely affected; for example, the ionic conductivity of the gel electrolyte, the switching speed of the electrochromic response, color contrast of the electrochromic response, adhesion of the gel electrolyte to the substrate, and flexibility of the electrodes.

In one embodiment, the gel electrolyte precursor mixture does not comprise a plasticizer. In another embodiment, the gel electrolyte does comprise a plasticizer.

The electrolyte composition may contain an ionic liquid. Ionic liquids are organic salts with melting points under about 100° C. Other ionic liquids have melting points of less than room temperature (~22° C.). Examples of ionic liquids that may be used in the electrolyte composition include imidazolium, pyridinium, phosphonium or tetralkylammonium based compounds, for example, 1-ethyl-3-methylimidazolium tosylate, 1-butyl-3-methylimidazolium octyl sulfate; 1-butyl-3-methylimidazolium 2-(2-methoxyethoxy)ethyl sulfate; 1-ethyl-3-methylimidazolium bis(pentafluoroethylsulfonyl) imide; 1-ethyl-3-methylimidazolium bis(trifluoromethylsulfonyl)imide; 1-ethyl-3-methylimidazolium bromide; 1-ethyl-3-methylimidazolium hexafluorophosphate; 1-butyl-3-methylimidazolium bromide; 1-butyl-3-methylimidazolium trifluoromethane sulfonate; 1,2-dimethyl-3-propylimidazolium tris(trifluoromethylsulfonyl)methide; 1,2-dimethyl-3-propylimidazolium bis(trifluoromethylsulfonyl)imide; 3-methyl-1-propylpyridinium bis(trifluormethylsulfonyl)imide; 1-butyl-3-methylpyridinium bis(trifluormethylsulfonyl)imide; 1-butyl-4-methylpyridinium chloride; 1-butyl-4-methylpyridinium hexafluorophosphate; 1-butyl-4-methylpyridinium tetrafluoroborate; 1-n-butyl-3-methylimidazolium hexafluorophosphate (n-BMIM $PF_6$); 1-butyl-3-methylimidazolium tetrafluoroborate (BMIM $BF_4$); phosphonium dodecylbenzenesulfonate; phosphonium methanesulfonate; and mixtures of these.

The amount of ionic liquid that can be used in the gel electrolyte precursor mixture can range from about 10% to about 80% by weight, specifically about 20% to about 70% by weight, more specifically about 30% to about 60% by weight, and yet more specifically about 40% to about 50% by weight of the gel electrolyte precursor mixture.

The gel electrolyte precursor can be converted to a gel via radical crosslinking initiated by thermal methods, or in particular by exposure to ultraviolet (UV) radiation. In an exemplary embodiment, the wavelength of UV irradiation is about 365 nm although other wavelengths can be used.

The gel electrolyte precursor mixture may comprise a thermal initiator or a photoinitiator. Exemplary photoinitiators include benzophenone, 2,2-dimethoxy-2-phenylacetophenone (DMPAP), dimethoxyacetophenone, xanthone, and thioxanthone. In one embodiment the initiator may include 2,2-dimethoxy-2-phenylacetophenone (DMPAP).

Crosslinking may also be thermally induced at about 40° C. to about 70° C., specifically about 50° C. using a thermal initiator. Exemplary thermal initiators include peroxide initiators such as benzyl peroxide (BPO), or azo bis isobutylnitrile (AIBN).

In one embodiment, the gel electrolyte precursor mixture comprises the electrolyte salt (e.g. metal salts, organic salts (e.g., ionic liquids), inorganic salts, or a combination thereof) and the gel precursor in a weight ratio of 1 to 10, with a 0.002 to 1 to 10 ratio of initiator to electrolyte to gel precursor, by weight.

Exemplary gel polymer electrolytes include those described in U.S. Pat. Nos. 7,586,663 and 7,626,748, both to Radmard et al.

The monomer composition generally comprises an electroactive monomer, a monomer composition solvent, and a monomer composition salt. The solvent can be the same type of solvent as described for optional use in polymer electrolyte matrix above. Exemplary solvent for use in the monomer composition include propylene carbonate, and the like. In one embodiment, the monomer composition salt is the same or similar to the salt used in the polymer electrolyte matrix and is present to avoid the salt concentration gradient between the bulk electrolyte and the monomer composition. This ensures the electroactive monomer as the only diffusing substance in the system without external bias.

The screening process can be used with solid or liquid electroactive monomers by selecting the appropriate solvent that would dissolve the electroactive monomer to form the monomer composition.

Examples of suitable electroactive monomers include those known in the art to exhibit electro activity when polymerized, including, for example, thiophene, substituted thiophene, carbazole, 3,4-ethylenedioxythiophene, thieno[3,4-b]thiophene, substituted thieno[3,4-b]thiophene, dithieno[3,4-b:3',4'-d]thiophene, thieno[3,4-b]furan, substituted thieno[3,4-b]furan, bithiophene, substituted bithiophene, pyrrole, substituted pyrrole, acetylene, phenylene, substituted phenylene, naphthalene, substituted naphthalene, biphenyl and terphenyl and their substituted versions, phenylene vinylene (e.g., p-phenylene vinylene), substituted phenylene vinylene, aniline, substituted aniline, indole, substituted indole, 2,2-dimethyl-3,4-propylenedioxythiophene, the monomers disclosed herein as structures (I)-(XXIX), combinations thereof, and the like.

The electroactive monomer can be selected from cathodically coloring materials, anodically coloring materials, or a combination thereof.

Cathodically coloring materials have a band gap ($E_g$) less than or equal to 2.0 eV in the neutral state. A cathodically coloring material changes color when oxidized (p-doped). The change in visible color can be from colored in the neutral state to colorless in the oxidized state, or from one color in the neutral state to a different color in the oxidized state. Cathodically coloring materials include, but are not limited to, polymers derived from a 3,4-alkylenedioxyheterocycle such as an alkylenedioxypyrrole, alkylenedioxythiophene or alkylenedioxyfuran. These further include polymers derived from 3,4-alkylenedioxyheterocycles comprising a bridge-alkyl substituted 3,4-alkylenedioxythiophene, such as 3,4-(2,2-dimethylpropylene)dioxythiophene (also referred to as 2,2-dimethyl-3,4-propylenedioxythiophene PropOT-$(Me)_2$), 3,4-(2,2-dihexylpropylene)dioxythiophene (PropOT-$(hexyl)_2$), or 3,4-(2,2-bis(2-ethylhexyl)propylene)dioxythiophene (PropOT-$(ethylhexyl)_2$). Herein, "colored" means the material absorbs one or more radiation wavelengths in the visible region (400 nm to 700 nm) in sufficient quantity that the reflected or transmitted visible light by the material is visually detectable to the human eye as a color (red, green, blue or a combination thereof).

An anodically coloring material has a band gap $E_g$ greater than 3.0 eV in its neutral state. An anodically coloring material changes color when reduced (n-doped). The material can be colored in the neutral state and colorless in reduced state, or have one color in the neutral state and a different color in the reduced state. An anodically coloring material can also comprise polymers derived from a 3,4-alkylenedioxyheterocycle or derived from an alkylenedioxyheterocycle such as alkylenedioxypyrrole, alkylenedioxythiophene or alkylenedioxyfuran. Exemplary 3,4-alkylenedioxyheterocycle monomers to prepare anodically coloring polymers include an N-alkyl substituted 3,4-alkylenedioxypyrrole, such as N-propyl-3,4-propylenedioxypyrrole (N-Pr PropOP), N-Gly-3,4-propylenedioxypyrrole (N-Gly PropOP), where N-Gly designates a glycinamide adduct of pyrrole group, or N-propane sulfonated PropOP (PropOP-NPrS).

Exemplary electroactive monomers include 3,4-ethylenedioxythiophene, 3,4-ethylenedithiathiophene, 3,4-ethylenedioxypyrrole, 3,4-ethylenedithiapyrrole, 3,4-ethylenedioxyfuran, 3,4-ethylenedithiafuran, and derivatives having the general structure (I):

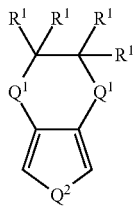

(I)

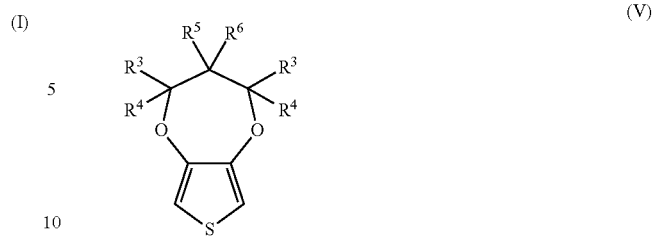

(V)

wherein each occurrence of $Q^1$ is independently S, O, or Se; $Q^2$ is S, O, or N—$R^2$ wherein $R^2$ is hydrogen or $C_1$-$C_6$ alkyl; and each occurrence of $R^1$ is independently hydrogen, $C_1$-$C_{12}$ alkyl, $C_1$-$C_{12}$ alkyl-OH, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl. In one embodiment, each occurrence of $R^1$ is hydrogen. In one embodiment, each $Q^1$ is O and $Q^2$ is S. In another embodiment, each $Q^1$ is O, $Q^2$ is S, and one $R^1$ is $C_1$-$C_{12}$ alkyl, $C_1$-$C_{12}$ alkyl-OH, $C_1$-$C_{12}$ haloalkyl, $C_1$-$C_{12}$ alkoxy, $C_1$-$C_{12}$ haloalkoxy, —$C_1$-$C_6$ alkyl-O—$C_1$-$C_6$ alkyl, while the remaining $R^1$ are hydrogen. In another embodiment, each $Q^1$ is O, $Q^2$ is S, and one $R^1$ is $C_1$ alkyl-OH, while the remaining $R^1$ are hydrogen. A specific electroactive monomer is 3,4-ethylenedioxythiophene or EDOT.

Another suitable electroactive monomer includes an unsubstituted and 2- or 6-substituted thieno[3,4-b]thiophene and thieno[3,4-b]furan having the general structures (II), (III), and (IV):

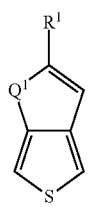

(II)

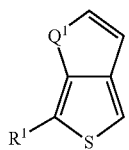

(III)

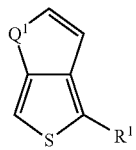

(IV)

wherein $Q^1$ is S, O, or Se; and $R^1$ is hydrogen, $C_1$-$C_{12}$ alkyl, $C_1$-$C_{12}$ haloalkyl including perfluoroalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl. In one embodiment, $Q^1$ is S and $R^1$ is hydrogen. In another embodiment, $Q^1$ is O and $R^1$ is hydrogen. In yet another embodiment, $Q^1$ is Se and $R^1$ is hydrogen.

Another suitable electroactive monomer includes substituted 3,4-propylenedioxythiophene (PropOT) monomers according to the general structure (V):

wherein each instance of $R^3$, $R^4$, $R^5$, and $R^6$ independently is hydrogen; optionally substituted $C_1$-$C_{20}$ alkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, —$C_1$-$C_{10}$ alkyl-aryl; or hydroxyl. The $C_1$-$C_{20}$ alkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, or —$C_1$-$C_{10}$ alkyl-aryl groups each may be optionally substituted with one or more of $C_1$-$C_{20}$ alkyl; aryl; halogen; hydroxyl; —N—$(R^2)_2$ wherein each $R^2$ is independently hydrogen or $C_1$-$C_6$ alkyl; cyano; nitro; —COOH; —S(=O) $C_0$-$C_{10}$ alkyl; or —S(=O)$_2$$C_0$-$C_{10}$ alkyl. In one embodiment, $R^5$ and $R^6$ are both hydrogen. In another embodiment, $R^5$ and $R^6$ are both hydrogen, each instance of $R^3$ independently is $C_1$-$C_{10}$ alkyl or benzyl, and each instance of $R^4$ independently is hydrogen, $C_1$-$C_{10}$ alkyl, or benzyl. In another embodiment, $R^5$ and $R^6$ are both hydrogen, each instance of $R^3$ independently is $C_1$-$C_5$ alkyl or benzyl and each instance of $R^4$ independently is hydrogen, $C_1$-$C_5$ alkyl, or benzyl. In yet another embodiment, each instance of $R^3$ and $R^4$ are hydrogen, and one of $R^5$ and $R^6$ is hydroxyl while the other is hydrogen.

Other suitable electroactive monomers include pyrrole, furan, thiophene, and derivatives having the general structure (VI):

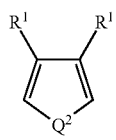

(VI)

wherein $Q^2$ is S, O, or N—$R^2$ wherein $R^2$ is hydrogen or $C_1$-$C_6$ alkyl; and each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl. An exemplary substituted pyrrole includes n-methylpyrrole. Exemplary substituted thiophenes include 3-methylthiophene and 3-hexylthiophene.

Additional electroactive monomers include isathianaphthene, pyridothiophene, pyrizinothiophene, and derivatives having the general structure (VII):

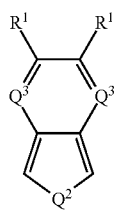

(VII)

wherein $Q^2$ is S, O, or N—$R^2$ wherein $R^2$ is hydrogen or $C_1$-$C_6$ alkyl; each occurrence of $Q^3$ is independently CH or N; and each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Still other electroactive monomers include oxazole, thiazole, and derivatives having the general structure (VIII):

(VIII)

wherein $Q^1$ is S or O.

Additional electroactive monomers include the class of compounds according to structure (IX):

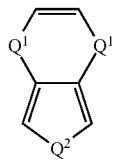

(IX)

wherein $Q^2$ is S, O, or N—$R^2$ wherein $R^2$ is hydrogen or $C_1$-$C_6$ alkyl; and each occurrence of $Q^1$ is independently S or O.

Additional electroactive monomers include bithiophene, bifuran, bipyrrole, and derivatives having the following general structure (X):

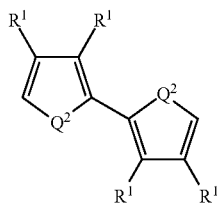

(X)

wherein each occurrence of $Q^2$ is independently S, O, or N—$R^2$ wherein $R^2$ is hydrogen or $C_1$-$C_6$ alkyl; and each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Other exemplary electroactive monomers include terthiophene, terfuran, terpyrrole, and derivatives having the following general structure (XI):

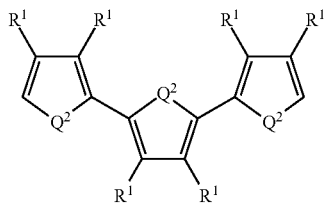

(XI)

wherein each occurrence of $Q^2$ is independently S, O, or N—$R^2$ wherein $R^2$ is hydrogen or $C_1$-$C_6$ alkyl; and each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Additional electroactive monomers include thienothiophene, thienofuran, thienopyrrole, furanylpyrrole, furanylfuran, pyrolylpyrrole, and derivatives having the following general structure (XII):

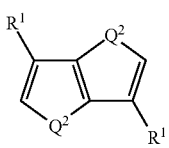

(XII)

wherein each occurrence of $Q^2$ is independently S, O, or N—$R^2$ wherein $R^2$ is hydrogen or $C_1$-$C_6$ alkyl; and each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Still other electroactive monomers include dithienothiophene, difuranylthiophene, dipyrrolylthiophene, dithienofuran, dipyrrolylfuran, dipyrrolylpyrrole, and derivatives having the following general structure (XIII):

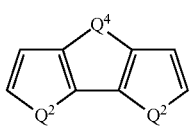

(XIII)

wherein each occurrence of $Q^2$ is independently S, O, or N—$R^2$ wherein $R^2$ is hydrogen or $C_1$-$C_6$ alkyl; $Q^4$ is $C(R^1)_2$, S, O, or N—$R^2$; and each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Additional electroactive monomers include dithienylcyclopentenone, difuranylcyclopentenone, dipyrrolylcyclopentenone and derivatives having the following general structure (XIV):

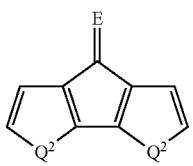

(XIV)

wherein each occurrence of $Q^2$ is independently S, O, or N—$R^2$ wherein $R^2$ is hydrogen or $C_1$-$C_6$ alkyl; and E is O or $C(R^7)_2$, wherein each occurrence of $R^7$ is an electron withdrawing group.

Other suitable electroactive monomers include those having the following general structure (XV):

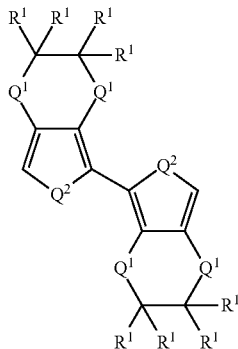

(XV)

wherein each occurrence of $Q^1$ is independently S or O; each occurrence of $Q^2$ is independently S, O, or N—$R^2$ wherein $R^2$ is hydrogen or $C_1$-$C_6$ alkyl; each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl. In one embodiment, each occurrence of $Q^1$ is O; each occurrence of $Q^2$ is S; and each occurrence of $R^1$ is hydrogen.

Additional electro active monomers include dithienovinylene, difuranylvinylene, and dipyrrolylvinylene according to the structure (XVI):

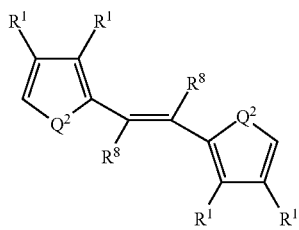

(XVI)

wherein each occurrence of $Q^2$ is independently S, O, or N—$R^2$ wherein $R^2$ is hydrogen or $C_1$-$C_6$ alkyl; each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl; and each occurrence of $R^8$ is hydrogen, $C_1$-$C_6$ alkyl, or cyano.

Other electroactive monomers include 1,2-trans(3,4-ethylenedioxythienyl)vinylene, 1,2-trans(3,4-ethylenedioxyfuranyl)vinylene, 1,2-trans(3,4-ethylenedioxypyrrolyl)vinylene, and derivatives according to the structure (XVII):

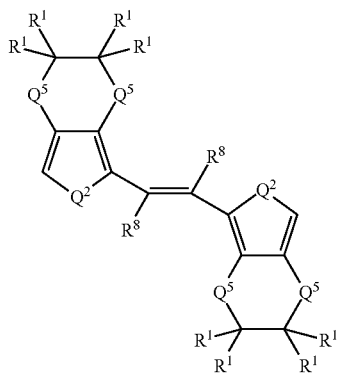

(XVII)

wherein each occurrence of $Q^5$ is independently $CH_2$, S, or O; each occurrence of $Q^2$ is independently S, O, or N—$R^2$ wherein $R^2$ is hydrogen or $C_1$-$C_6$ alkyl; each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl; and each occurrence of $R^8$ is hydrogen, $C_1$-$C_6$ alkyl, or cyano.

Additional electroactive monomers include the class bis-thienylarylenes, bis-furanylarylenes, bis-pyrrolylarylenes and derivatives according to the structure (XVIII):

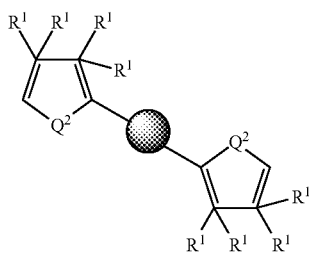

(XVIII)

wherein each occurrence of $Q^2$ is independently S, O, or N—$R^2$ wherein $R^2$ is hydrogen or $C_1$-$C_6$ alkyl; each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl; and

represents an aryl. Exemplary aryl groups include furan, pyrrole, N-substituted pyrrole, phenyl, biphenyl, thiophene, fluorene, 9-alkyl-9H-carbazole, and the like.

Other electroactive monomers include the class of bis(3,4-ethylenedioxythienyl)arylenes, related compounds, and derivatives according to the structure (XIX):

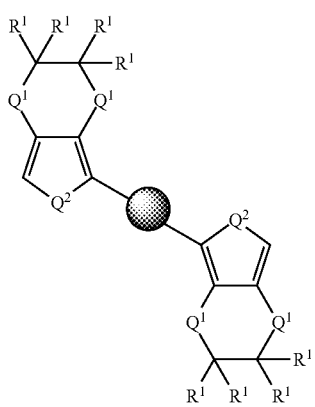

(XIX)

wherein each occurrence of $Q^1$ is independently S or O; each occurrence of $Q^2$ is independently S, O, or N—$R^2$ wherein $R^2$ is hydrogen or $C_1$-$C_6$ alkyl; each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl; and

represents an aryl.

Other exemplary electroactive monomers include bis(3,4-ethylenedioxythienyl)arylenes according to structure (XIX) includes the compound wherein all $Q^1$ are O, both $Q^2$ are S, all $R^1$ are hydrogen, and

is phenyl linked at the 1 and 4 positions. Another exemplary compound is where all $Q^1$ are O, both $Q^2$ are S, all $R^1$ are hydrogen, and

is thiophene linked at the 2 and 5 positions (bisEDOT-thiophene).

Additional electroactive monomers include the class of compounds according to structure (XX):

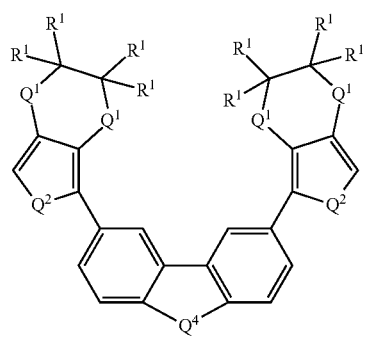

(XX)

wherein each occurrence of $Q^1$ is independently S or O; each occurrence of $Q^2$ is independently S, O, or N—$R^2$ wherein $R^2$ is hydrogen or $C_1$-$C_6$ alkyl; $Q^4$ is $C(R^1)_2$, S, O, or N—$R^2$; and each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl. In one embodiment, each occurrence of $Q^1$ is O; each occurrence of $Q^2$ is S; each occurrence of $R^1$ is hydrogen; and $R^2$ is methyl.

Still other electroactive monomers include the class of compounds according to structure (XXI):

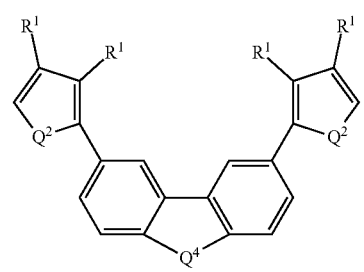

(XXI)

wherein each occurrence of $Q^2$ is independently S, O, or N—$R^2$ wherein $R^2$ is hydrogen or $C_1$-$C_6$ alkyl; $Q^4$ is $C(R^1)_2$, S, O, or N—$R^2$; and each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Additional electroactive monomers include the class of compounds according to structure (XXII):

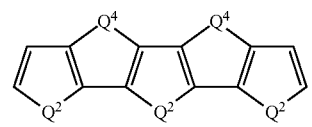

(XXII)

wherein each occurrence of $Q^2$ is independently S, O, or N—$R^2$ wherein $R^2$ is hydrogen or $C_1$-$C_6$ alkyl; each occurrence of $Q^4$ is $C(R^1)_2$, S, O, or N—$R^2$; and each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Other exemplary monomers include the class of compounds according to structure (XXIII):

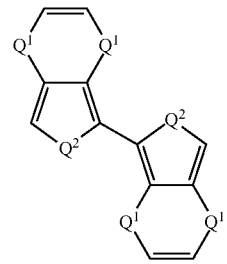

(XXIII)

wherein each occurrence of $Q^2$ is independently S, O, or N—$R^2$ wherein $R^2$ is hydrogen or $C_1$-$C_6$ alkyl; and each occurrence of $Q^1$ is independently S or O.

Exemplary electroactive monomers include the class of compounds according to structure (XXIV):

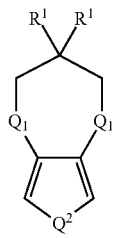

(XXIV)

wherein $Q^2$ is S, O, or N—$R^2$ wherein $R^2$ is hydrogen or $C_1$-$C_6$ alkyl; each occurrence of $Q^1$ is independently S or O; and each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, —$C_1$-$C_6$ alkyl-aryl, —$C_1$-$C_6$ alkyl-O-aryl, or —$C_1$-$C_6$ alkyl-O-aryl. In one embodiment, one $R^1$ is methyl and the other $R^1$ is benzyl, —$C_1$-$C_6$ alkyl-O-phenyl, —$C_1$-$C_6$ alkyl-O-biphenyl, or —$C_1$-$C_6$ alkyl-biphenyl.

Additional electroactive monomers include the class of compounds according to structure (XXV):

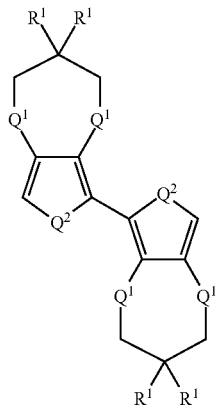

(XXV)

wherein each occurrence of $Q^2$ is independently S, O, or N—$R^2$ wherein $R^2$ is hydrogen or $C_1$-$C_6$ alkyl; each occurrence of $Q^1$ is independently S or O; and each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl. In one embodiment, one $R^1$ is methyl and the other $R^1$ is —$C_1$-$C_6$ alkyl-O-phenyl or —$C_1$-$C_6$ alkyl-O-biphenyl per geminal carbon center.

Other electroactive monomers include the class of compounds according to structure (XXVI):

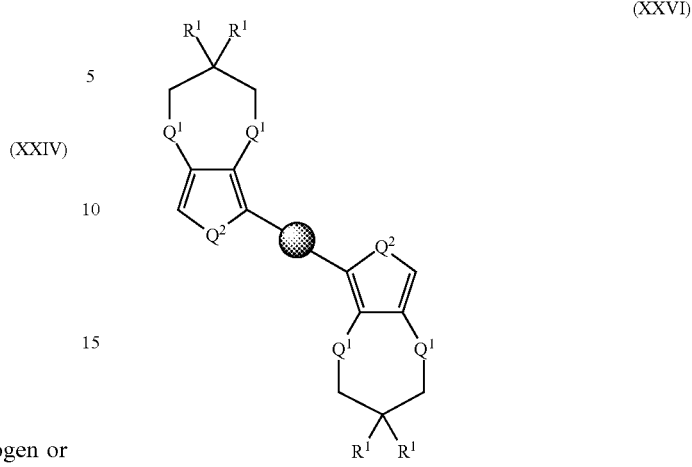

(XXVI)

wherein each occurrence of $Q^2$ is independently S, O, or N—$R^2$ wherein $R^2$ is hydrogen or $C_1$-$C_6$ alkyl; each occurrence of $Q^1$ is independently S or O; each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl; and represents an aryl. In one embodiment, one $R^1$ is methyl and the other $R^1$ is —$C_1$-$C_6$ alkyl-O-phenyl or —$C_1$-$C_6$ alkyl-O-biphenyl per geminal carbon center.

Exemplary electroactive monomers include the class of compounds according to structure (XXVII):

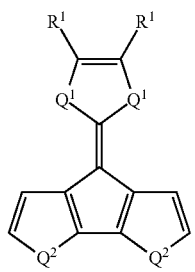

(XXVII)

wherein each occurrence of $Q^2$ is independently S, O, or N—$R^2$ wherein $R^2$ is hydrogen or $C_1$-$C_6$ alkyl; each occurrence of $Q^1$ is independently S or O; and each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Additional electroactive monomers include the class of compounds according to structure (XXVIII):

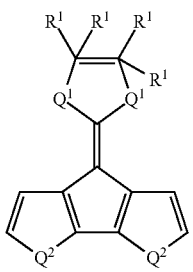

(XXVIII)

wherein each occurrence of $Q^2$ is independently S, O, or N—$R^2$ wherein $R^2$ is hydrogen or $C_1$-$C_6$ alkyl; each occurrence of $Q^1$ is independently S or O; and each occurrence of $R^1$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Another electroactive monomer includes aniline or substituted aniline according to structure (XXIX):

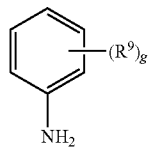

(XXIX)

wherein g is 0, 1, 2, or 3; and each occurrence of $R^9$ is independently $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, —$C_1$-$C_6$ alkyl-O-aryl, or N—$R^2$ wherein $R^2$ is hydrogen or $C_1$-$C_6$ alkyl.

Color tuning can be achieved by the choice of monomers for copolymerization.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, "—CHO" is attached through carbon of the carbonyl group.

Unless otherwise indicated, the term "substituted" as used herein means replacement of one or more hydrogens with one or more substituents. Suitable substituents include, for example, hydroxyl, $C_6$-$C_{12}$ aryl, $C_3$-$C_{20}$ cycloalkyl, $C_1$-$C_{20}$ alkyl, halogen, $C_1$-$C_{20}$ alkoxy, $C_1$-$C_{20}$ alkylthio, $C_1$-$C_{20}$ haloalkyl, $C_6$-$C_{12}$ haloaryl, pyridyl, cyano, thiocyanato, nitro, amino, $C_1$-$C_{12}$ alkylamino, $C_1$-$C_{12}$ aminoalkyl, acyl, sulfoxyl, sulfonyl, amido, or carbamoyl.

As used herein, "alkyl" includes straight chain, branched, and cyclic saturated aliphatic hydrocarbon groups, having the specified number of carbon atoms, generally from 1 to about 20 carbon atoms, greater than 3 for the cyclic. Alkyl groups described herein typically have from 1 to about 20, specifically 3 to about 18, and more specifically about 6 to about 12 carbons atoms. Examples of alkyl include, but are not limited to, methyl, ethyl, n-propyl, isopropyl, n-butyl, 3-methylbutyl, t-butyl, n-pentyl, and sec-pentyl. As used herein, "cycloalkyl" indicates a monocyclic or multicyclic saturated or unsaturated hydrocarbon ring group, having the specified number of carbon atoms, usually from 3 to about 10 ring carbon atoms. Monocyclic cycloalkyl groups typically have from 3 to about 8 carbon ring atoms or from 3 to about 7 carbon ring atoms. Multicyclic cycloalkyl groups may have 2 or 3 fused cycloalkyl rings or contain bridged or caged cycloalkyl groups. Examples of cycloalkyl groups include cyclopropyl, cyclobutyl, cyclopentyl, or cyclohexyl as well as bridged or caged saturated ring groups such as norbornane or adamantane.

As used herein "haloalkyl" indicates both branched and straight-chain alkyl groups having the specified number of carbon atoms, substituted with 1 or more halogen atoms, generally up to the maximum allowable number of halogen atoms ("perhalogenated"). Examples of haloalkyl include, but are not limited to, trifluoromethyl, difluoromethyl, 2-fluoroethyl, and penta-fluoroethyl.

As used herein, "alkoxy" includes an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Haloalkoxy" indicates a haloalkyl group as defined above attached through an oxygen bridge.

As used herein, the term "aryl" indicates aromatic groups containing only carbon in the aromatic ring or rings. Such aromatic groups may be further substituted with carbon or non-carbon atoms or groups. Typical aryl groups contain 1 or 2 separate, fused, or pendant rings and from 6 to about 12 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

As used herein "heteroaryl" indicates aromatic groups containing carbon and one or more heteroatoms chosen from N, O, and S. Exemplary heteroaryls include oxazole, pyridine, pyrazole, thiophene, furan, isoquinoline, and the like. The heteroaryl groups may be substituted with one or more substituents.

As used herein, "halo" or "halogen" refers to fluoro, chloro, bromo, or iodo.

As used herein, "arylene" includes any divalent aromatic hydrocarbon or two or more aromatic hydrocarbons linked by a bond, a heteroatom (e.g., O, S, S(═O), S(═O)$_2$, etc.), a carbonyl group, an optionally substituted carbon chain, a carbon chain interrupted by a heteroatom, and the like.

The screening device may further include a variety of substrate materials (flexible or rigid) used to house the electrolyte/monomer combination. Exemplary substrate materials include glass, plastic, silicon, a mineral, a semiconducting material, a ceramic, a metal, and the like, as well as a combination thereof. The substrate may be inherently conductive. Flexible substrate layers can be made from plastic. Exemplary plastics include polyethylene terephthalate (PET), poly (arylene ether), polyamide, polyether amide, etc. The substrate may include mirrored or reflective substrate material.

Exemplary electrode materials for use in the devices can include inorganic materials such as glass-indium doped tin oxide (glass-ITO), doped silicon, metals such as gold, platinum, aluminum, and the like, metal alloys such as stainless steel ("SS"), SS 316, SS316L, nickel and/or cobalt alloys such as Hastelloy-B® (Ni62/Mo28/Fe5/Cr/Mn/Si), Hastelloy-C®, and the like; and organic materials such as a conjugated polymer such as poly(3,4-ethylenedioxythiophene)-polystyrene sulfonate (PEDOT-PSS), conjugated polymers prepared from an electroactive monomer described herein, carbon black, carbon nanotubes, graphene, and the like.

In one embodiment, all of the electrodes are polyethylene terephthalate (PET)/indium-doped tin oxide (ITO) substrates.

The screening device can generally be fabricated by positioning a polymer electrolyte matrix between at least two electrodes, wherein the electrodes are in electrical communication with the electrolyte. The screening device comprises one, two, or more (e.g. a plurality) of reservoirs in the polymer electrolyte matrix to receive a monomer composition. The electroactive monomer of the monomer composition is allowed to diffuse into the surrounding polymer electrolyte matrix of the screening device. After a set time point the electroactive monomer is polymerized and the distance the monomer traveled is determined. In one embodiment, the electroactive monomer is polymerized in the assembled device by applying voltage (oxidative potential) across the device. The electroactive monomer irreversibly converts to a conjugated polymer and can be switched as normal. In another embodiment, the electroactive monomer is polymerized by exposure to bromine vapor.

The electrolyte composition can be formed into a layer in the screening device by applying the mixture to a substrate via conventional processes including ink jet printing, screen printing, roll to roll printing processes, reel to reel processing, spin coating, meniscus and dip coating, spray coating, brush coating, doctor blade application, curtain casting, drop casting, and the like.

The polymerization of the electroactive monomers can be effected by cyclic voltammetry (triangle wave voltammetry), chronocoulometry/constant voltage, galvanostatic/constant current, or square-wave voltammetry (pulsed). In several embodiments, a reference electrode is fabricated inside the device. The potential (voltage) is applied to one electrode of the device for a sufficient time to substantially deplete the monomer from the combination of polymer electrolyte matrix and electroactive monomer composition. The formation of the conjugated polymer occurs on one electrode side, via diffusion through the electrolyte matrix. In one embodiment, the conjugated polymer is not a discrete, thin film layer, as can be formed using electrodeposition methods, but rather is a blend or composite within the polymer electrolyte matrix.

In several embodiments, the device comprises an internal reference electrode system to result in a three-electrode cell. In one embodiment, the internal reference electrode is a silver wire pseudo-reference electrode embedded within the device to control voltage and prevent electrode damage (e.g., ITO degradation due to over-oxidation).

In another embodiment, a sealing means (e.g. a gasket) is provided between two substrates or electrodes to form an electrochromic device wherein an internal reference electrode is provided between the sealing means. The sealing means seals the device.

The devices can be sealed to prevent water, air, or other contaminant materials from entering the device, as well as to prevent loss of electrolyte composition/electroactive monomer or electrolyte composition/conjugated polymer. Sealing can be accomplished using an adhesive such as a polyurethane based UV curable resin or other suitable adhesive used in the formation of electrochromic devices.

Knowledge of the monomer diffusion allows for precise calculation of the monomer feed ratio to generate the color of interest for an electrochromic device. The high-throughput screening method was verified by preparation of electrochromic devices by pinpointing a color coordinate obtained from the screening technique and using the calculated composition to generate the desired color of the electrochromic device. Thus, the process disclosed herein can be used to accelerate the color selection process for electrochromic devices and display applications. Specific articles prepared from the electrochromic devices include eyewear such as color-changing sunglasses, high-contrast sunglasses or goggles, windows devised for heat-modulation in skyscrapers/buildings or fashion-tinting, auto-dimming mirrors in automobiles and trucks, displays, or a variety of other color-changing devices.

In one embodiment, a method for screening comprises:
a.) providing a screening device comprising at least two electrodes and a polymer electrolyte matrix disposed between the at least two electrodes, wherein the polymer electrolyte matrix comprises a plurality of reservoirs;
b.) providing an electroactive monomer composition in the plurality of reservoirs, wherein the electroactive monomer composition comprises an electroactive monomer of a known concentration, a monomer composition solvent, and a monomer composition salt, wherein each reservoir comprises a single electroactive monomer composition;
c.) allowing the electroactive monomer of the electroactive monomer composition to diffuse through the polymer electrolyte matrix for a period of time;
d.) polymerizing the electroactive monomer by applying a voltage to the device to form a conjugated polymer within the polymer electrolyte matrix or a conjugated copolymer where at least two electroactive monomers have diffused into the same area of the polymer electrolyte matrix;
e.) determining the diffusion behavior of the monomer in the monomer compositions;
f.) obtaining the CIELuv color coordinates of the conjugated polymer or conjugated copolymer;
g) correlating the color coordinates of the conjugated copolymers with monomer feed ratios; and optionally predicting the composition of electroactive monomers to achieve a select color.

The following illustrative examples are provided to further describe the invention and are not intended to limit the scope of the claimed invention.

EXAMPLES

Example 1

In Situ Polymerization of EDOT in an Assembled Solid-State Device

Polymer Electrolyte: Five grams (g) of propylene carbonate, 5 g of poly(ethylene glycol)diacrylate (Mn=700), 1 g of lithium trifluoromethanesulfonate ("Litrif"), and 17.5 milligrams (mg) of dimethoxyphenylacetophenone ("DMPAP") were added together and sonicated for 15 minutes until dissolved. The electrolyte is a colorless to light yellow liquid before UV exposure and a transparent gel afterwards. All chemicals were purchased from Sigma-Aldrich and used as received.

Device Assembly: A rubber gasket was glued between two pieces of ITO coated polyethylene terephthalate. Rectangular holes were carved on the top substrate and rubber parts were fitted into the holes. Gel electrolyte was filled into the gasket and cured by 365 nm UV light. After curing, the small rubber parts were removed from the holes and formed two reservoirs in the solid-state device. Monomer solutions (50% wt:wt monomer:solution) were put in these reservoirs and were allowed to diffuse for time periods described below. At the end of these periods, the leftover solutions were taken out and the electroactive monomers in the gel electrolyte matrix were polymerized either by bromine exposure or electropolymerization. In the case of electropolymerization, a potential of 3V was applied to the device for 30 s and −2 V to +2 V was used for switching. Electrochemistry was carried out using CHI 400 and 660 A potentiostats. Color characterizations were carried out with a PR-670 SpectroScan Spectroradiometer (Photo Research, Inc.).

Monomers and Monomer Diffusion Rates: Fifty % 3,4-ethylenedioxythiophene ("EDOT") in propylene carbonate containing 0.1M Litrif was used as the reservoir filling, which was allowed different diffusion time periods ranging from 2 hours to 24 hours. Litrif salt was added to the monomer composition to avoid the salt concentration gradient between the bulk gel electrolyte and the monomer solution. This ensured the monomer as the only diffusing substance in the system without external bias. The distance EDOT travelled was measured by tracing the blue color after its conversion to PEDOT. Processes such as electrochemical conversion by applying a +3V potential or bromine vapor exposure can be used to polymerize the electroactive monomer. Although it was found that the result was not affected by which polymerization route was used, electropolymerization is a more convenient approach due to the fact that bromine conversion requires the top ITO electrode to be removed from the device to allow exposure to bromine vapor. The resulting one electrode system makes it difficult to switch the color back. The devices prepared from elctropolymerization do not need to be dissembled and color can be switched afterwards. Also, the intense color of bromine vapor is prone to stay in the gel electrolyte and interferes with the color of the copolymers. Both tests gave a diffusion distance of 1.9 millimeters (mm) after 3 hours.

FIG. 1A is a schematic illustration of the device with a rectangular-shaped reservoir for monomer solution in the center; (B) the circled region illustrates the diffusion of the monomer EDOT, which is colorless but was marked shading in the Figure for clarity; (C) the diffusion radius can be observed by the color of the polymerized EDOT in the reduced (C) and oxidized (D) states. To quantitatively characterize the diffusion behavior of different monomers, model electroactive monomers pyrrole, EDOT, 2,2-dimethyl-3,4-propylenedioxythiophene ("DMP" or "Pro-DOT-Me$_2$"), and bithiophene ("BiTh") were used.

As the monomer diffuses from the reservoir into the surrounding polymer electrolyte matrix, the concentration gradient decreases with increasing distance from the reservoir, i.e. the process is a non-steady-state diffusion of which the behavior can be described by Fick's second law.

$$x=\sqrt{2Dt} \quad \text{Equation 1}$$

Where x is the distance the electroactive monomer travelled from the reservoir (e.g. in meters), D is the diffusion coefficient (e.g. in meter$^2$/seconds), t is the time of the diffusion (e.g. in seconds). According to Fick's law, diffusion coefficient follows Equation 1 at a short time scale, and remains constant through the diffusion process. Diffusion was terminated at various times (up to 24 hours), the electroactive monomer was subsequently polymerized, and D was calculated based on the distance the electroactive monomer travelled in time t using Equation 1, as summarized in Table 1 for each electroactive monomer with different concentrations. Diffusion coefficient increases with initial electroactive monomer concentration and is inversely proportional to the electroactive monomer molecule size. For example, the largest molecule used in this study, DMP, only travelled 1.9 mm after 15 hours.

TABLE 1

Diffusion coefficient for different electroactive monomers at various concentrations.

| Monomer | D (m$^2$/s) |
|---|---|
| 100% EDOT | 2.97E−10 |
| 50% EDOT | 1.91E−10 |
| 20% EDOT | 1.14E−10 |
| 2.5% EDOT | 9.57E−11 |
| 50% Pyrrole | 2.95E−9 |
| 2.5% Pyrrole | 2.95E−9 |
| 50% DMP | 1.04E−10 |
| 50% Bithiophene | 2.58E−10 |
| 25% ProDOT-Me$_2$ | 3.58E−11 |
| 50% ProDOT-Me$_2$ | 2.77E−11 |
| ProDOT-Me$_2$ | 1.21E−11 |
| ProDOT-tBu$_2$ | 4.63E−12 |

Figure 2:
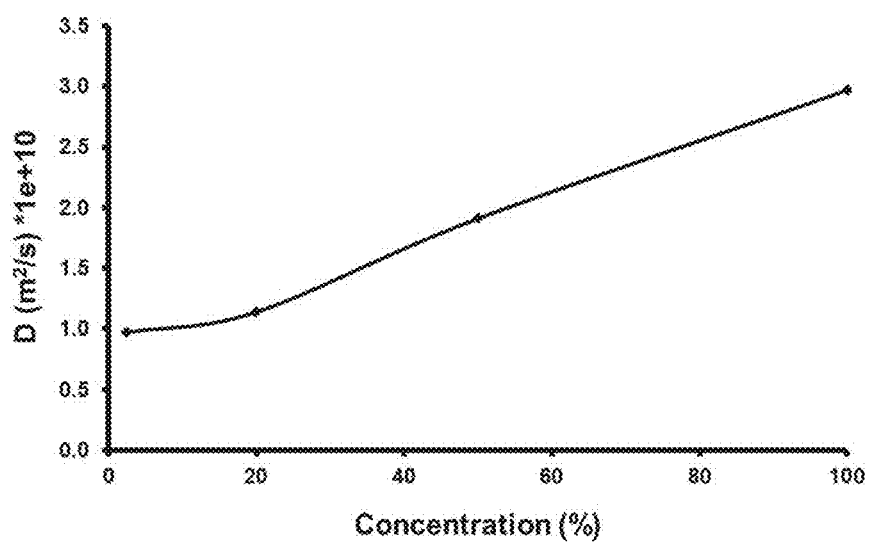
FIG. 2 graphically illustrates the correlation between the initial EDOT monomer concentration (expressed in weight % in stock solution) and diffusion coefficient D.
Figures 3A, 3B, 3C, 3D:
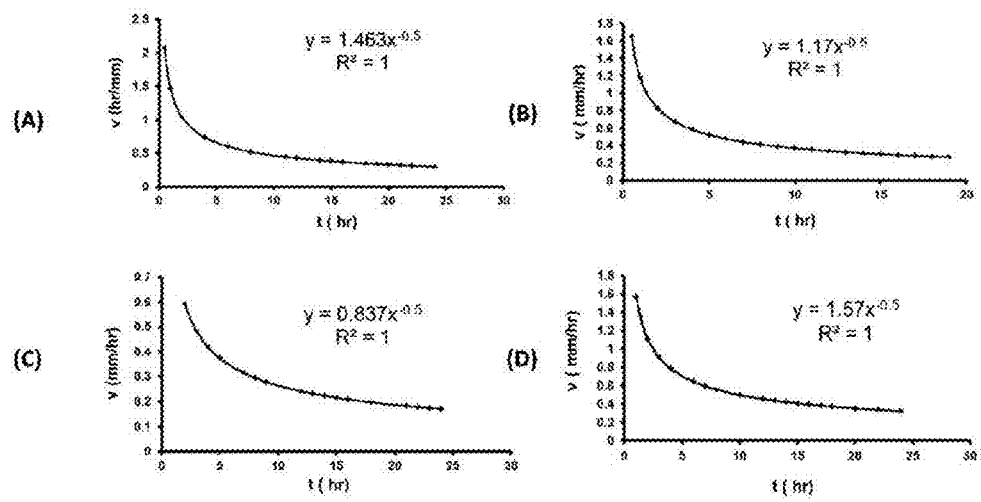
FIGS. 3A, 3B, 3C, and 3D: Plots of diffusion rate versus time of (A) 100% EDOT; (B) 50% EDOT; (C) 2.5% EDOT and (D) 50% bithiophene.

The correlation between the initial concentration and D value of EDOT is depicted in FIG. 2. Although there has been no conclusive equation for the relation between concentration and D, in the case of 50% EDOT, they have a near linear correlation. The diffusion kinetics can be expressed in diffusion rate obtained by the slope of travel distance x versus travel time, as shown in FIG. 3A-C. The diffusion rate decreases as the electroactive monomer travels further into the polymer electrolyte matrix accompanied with decreasing concentration gradient, which was expected due to less driving force.

Figures 4A, 4B:
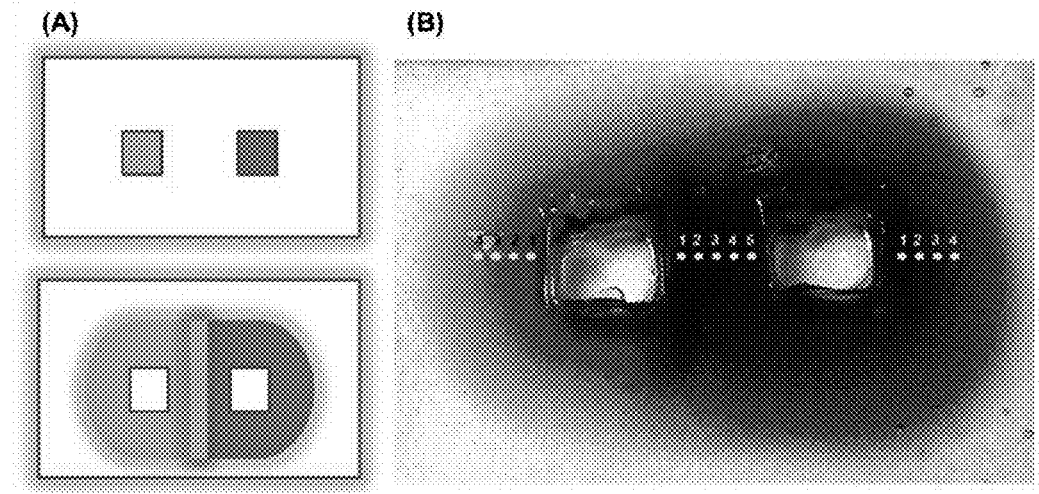
FIGS. 4A and 4B.

Copolymerization and High Throughput Color Screening Platform: Using the information of the diffusion behavior of individual electroactive monomers, copolymerization is used to design a high throughput color screening platform. Two concepts are used in the design: 1) saturation point, the point where diffusion is so slow that it is negligible in the time scale of the study; 2) saturation distance, the farthest distance the electroactive monomer travels at saturation point. Saturation distance of an electroactive monomer is useful in the color screening process because when two monomers are used in the copolymerization design (FIG. 4A), monomers with similar saturation distances will allow the maximum blending of the two. That is, there is an overlap of codiffusion of the monomers. In addition, a proper distance between the two reservoirs is determined by the saturation distance of two electroactive monomers. At the saturation point, the electroactive monomers were polymerized and copolymers were formed where the two monomers were mixed. FIG. 4A is a schematic of a high throughput color selection device setup. FIG. 4B shows the neutral state of the copolymer device of 50% EDOT and 50% bithiophene diffusion system. The distance between each point is 1 mm.

The feeding ratio of the copolymerization depends on the electroactive monomer concentration distribution at this point. The feeding concentration can be calculated by Equation 2, a derivation of Fick's second law.

$$c=c_2 * \text{erfc} * (y/2\sqrt{Dt_{sp}}) \quad \text{Equation 2}$$

Where y is the distance of the point of interest from the reservoir, D is the diffusion coefficient, $t_{sp}$ is the time needed to reach saturation point, c is the concentration at distance y, $c_2$ is the initial concentration, i.e., the concentration of the electroactive monomer solution in the reservoir, and erfc is a Guassian function called "error function", the value of error function can be found from literature and handbooks. For proof of concept, 50% EDOT and 50% bithiophene were chosen as a model for copolymerization, since they have similar Ds and saturation distances. Also, the distinctive colors of these two conductive polymers in neutral states (dark blue for PEDOT and orange red for polythiophene) make them ideal for color characterizations. Table 2 summarizes the concentration distribution of 50% EDOT and 50% bithiophene along the diffusion path, and shows the composition transition from bithiophene-dominant to EDOT-dominant from left to right between the two reservoirs. The diffusion behaviors of the electroactive monomers were proven to be independent and therefore not interfering with each other when mixed (See Example 2 below).

TABLE 2

Electroactive monomer feeding concentrations calculated from Equation. 2. Points correspond to the yellow points numbered in FIG. 4B.

| | BiTh (left) | | Copolymer | | EDOT (right) | |
|---|---|---|---|---|---|---|
| | BiTh % | EDOT % | BiTh % | EDOT % | BiTh % | EDOT % |
| 1 | 41.60 | 0 | 41.60 | 11.75 | 0 | 40.70 |
| 2 | 33.55 | 0 | 33.55 | 17.15 | 0 | 32.00 |
| 3 | 26.25 | 0 | 26.25 | 24.00 | 0 | 24.00 |
| 4 | 21.40 | 0 | 21.40 | 32.00 | 0 | 17.15 |
| 5 | | | 14.45 | 40.70 | | |

Figure 5:
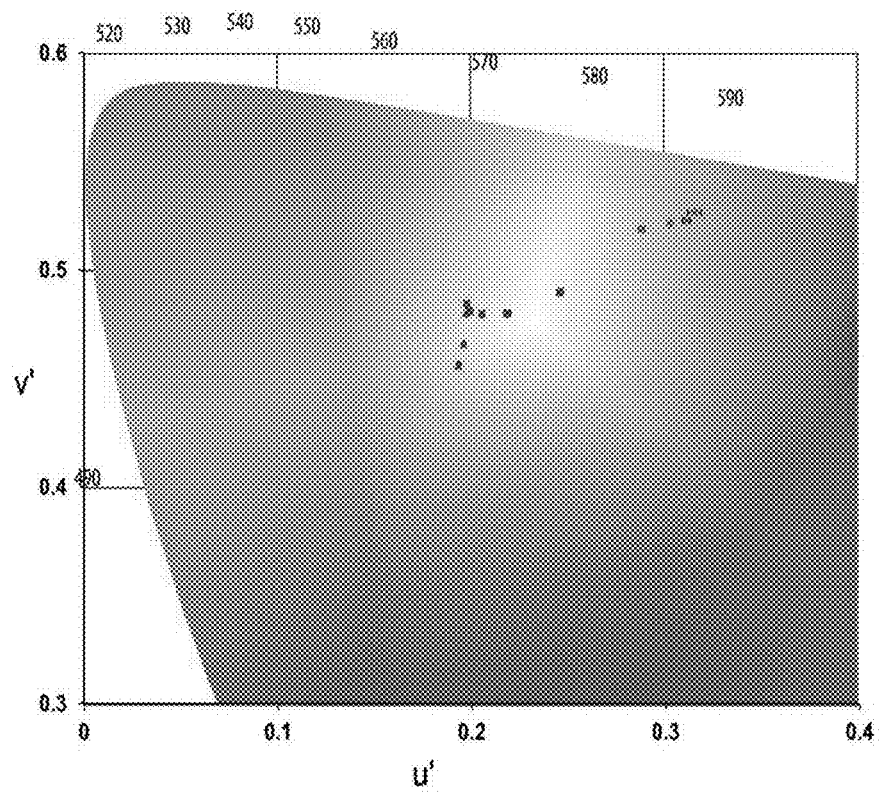
FIG. 5 Color coordinates of the points in FIG. 4B: PEDOT (triangle), polythiophene (diamond), copolymer of the two (square).

The relation between the electroactive monomer feeding ratios and electropolymerized copolymer composition was determined. To establish the correlation between a particular color and an unknown composition, colors of electrochromic polymers are to be characterized accurately. In the present study CIELuv color coordinates were used to characterize the color differences. CIELuv color space is published by the Commission Internationale de L'éclairage to numerically express color perceptions. Colors were characterized by a set of value of u' and v', L represents the luminosity of the sample and is not reflected in the color space graph. For example, a PEDOT device assembled by in situ approach with a 2.5% EDOT loading has a value of u'=0.1953, v'=0.4587 at 5 s and reaches u'=0.1906, v'=0.4060 at 30 s conversion. With the changing u' v' values the data point moves to deeper blue region in the color space, corresponds to what the eyes perceive. In the case of 50% EDOT and 50% bithiophene copolymerization, after polymerized in situ, as shown in FIG. 4B and switched to the neutral state, color coordinates were collected at various points at 1 mm intervals (FIG. 5, points labelled in FIG. 4B).

Figure 6:
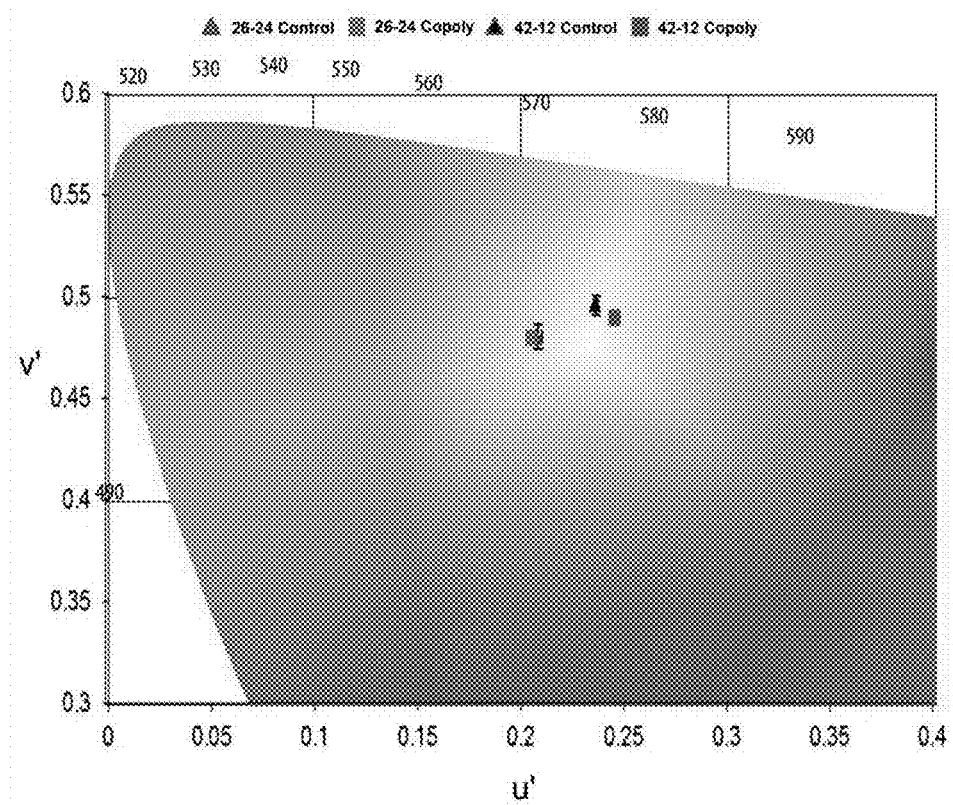
FIG. 6 Color coordinates of control devices and those made with the diffusion-copolymerization approach.

To test the color accuracy of the diffusion-copolymerization approach of the screening method, two compositions, 26% bithiophene with-24% EDOT and 42% bithiophene with 12% EDOT, respectively, were chosen as control groups. Control devices were fabricated using the unmodified in situ assembly approach: gel electrolyte mixed with the electroactive monomers was sandwiched between electrodes, UV cured and converted. Color coordinates were measured and compared with those obtained from the copolymerization approach. The colors of 26%-24% feed of two approaches overlaps with each other while the 42%-12% pair has a slight deviation. It is worth noting that to precisely reproduce the colors, the thickness (or equivalent thickness) of the films in the device also needs to be matched. In the high throughput screening process, a rubber gasket was used, it is a thicker device than that in normal practice; in addition, the gel electrolyte was crosslinked before electroactive monomer entering the system. For the control group, the electroactive monomer was mixed with the gel before crosslinking which may affect the thickness of the polymer layer and the color outcome. The color match determination of FIG. 6 was before any correction of these factors and may be the reason for the slight offset. Justification of these effects can be done by calculating the charge consumed in polymerization or by obtaining a calibration curve of the absorption-thickness relation for the system.

Example 2

Independence of the Electroactive Monomer Diffusion Behavior

The effect of the presence of another electroactive monomer on the diffusion behavior of a first electroactive monomer was tested by using the same device structure described in Example 1. However, instead of pure gel electrolyte, EDOT was added and mixed with the gel electrolyte before curing. Bithiophene stock solution was then used to fill the reservoir, diffused into EDOT-containing gel electrolyte and then both monomers were polymerized. The D value of bithiophene in EDOT-containing gel electrolyte is the same as the value obtained in pure electrolyte matrix and therefore confirmed the independence of the diffusion behavior of the electroactive monomers.

Example 3

Study of Three Copolymer Systems Prepared from Monomers of Varying Color

Three systems were studied prepared from monomers of various colors: PropOT-Me$_2$ to 1,3-di-tert-butyl-3,4-propylenedioxythiophene (PropOT-tBu$_2$), EDOT to bithiophene, and PropOT-Me$_2$ to bithiophene. The distinctive colors of the four conjugated polymers prepared from the individual monomers are provided in Table 3.

TABLE 3

| Polymer | Monomer | Neutral state color | Oxidized state color |
|---|---|---|---|
| PEDOT | 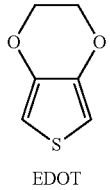<br>EDOT | Dark blue | Light blue |
| polybithiophene | 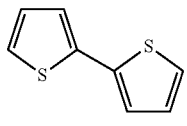<br>bithiophene | Orange | Blue-gray |
| polyProDOT-Me$_2$ | 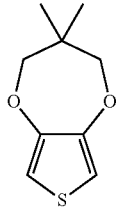<br>ProDOT-Me$_2$ | Dark blue | Transparent |

TABLE 3-continued

| Polymer | Monomer | Neutral state color | Oxidized state color |
|---|---|---|---|
| polyProDOT-tBu$_2$ | ProDOT-tBu$_2$ | Yellow | Transparent |

System 1 contained two monomers that in the colored state are dark blue (PropOT-Me$_2$) and yellow (PropOT-tBu$_2$) which one would expect to produce green in the copolymer region, but the results produce several colors including the primary color red (point 5 u' 0.439, v' 0.516). However, the copolymer region does not show green color. The concentration of the monomers studied in this system were 5% PropOT-Me$_2$ and 5% PropOT-tBu$_2$. As the non-polar PropOT-tBu$_2$ monomer is only partially soluble in the polar solvent, propylene carbonate, at this percentage, the actual concentration that diffuses is slightly less than 5% due to some of the monomer falling out of solution. The copolymer region is closest to PropOT-tBu$_2$ reservoir due to the steric hindrance of the t-butyl groups on PropOT-tBu$_2$ causing a slower diffusion rate compared to the less sterically hindered methyl groups on PropOT-Me$_2$. The copolymer region showed several colors including purple, pink, red, brown, and orange. The reason for this gradient of colors is due to the change of the monomer feed ratio at each point, and hence a change in the amount of each respective monomer within the backbone of the conjugated copolymer. Each different copolymer will have a different band gap. The monomer feed ratios for polyPropOT-Me$_2$ and polyPropOT-tBu$_2$ are shown in Table 4. at each 0.1 mm point between the reservoirs calculated from Equation 2. In their oxidized states, they are completely transparent which is of significant importance for use in display and eyewear applications.

TABLE 4

| Point between reservoirs | Feed Ratio ProDOT-Me$_2$: ProDOT-tBu$_2$ | u' | v' |
|---|---|---|---|
| 1 | 2.97:0.02 | 0.227 | 0.383 |
| 2 | 2.5:0.03 | 0.255 | 0.407 |
| 3 | 2.1:0.05 | 0.395 | 0.478 |
| 4 | 1.8:0.1 | 0.426 | 0.513 |
| 5 | 1.5:0.19 | 0.439 | 0.516 |
| 6 | 1.35:0.36 | 0.404 | 0.528 |
| 7 | 1.15:0.69 | 0.341 | 0.536 |
| 8 | 0.98:1.32 | 0.310 | 0.539 |
| 9 | 0.84:2.51 | 0.288 | 0.542 |
| 10 | 0.72:4.7 | 0.238 | 0.521 |
|  | 100:0 | 0.169 | 0.192 |
|  | 0:100 | 0.24 | 0.518 |

* Distance between each point is about 0.1 mm.

The study with PropOT-tBu$_2$ and PropOT-Me$_2$ shows that if each of two homopolymers generated from each of the two respective monomers exhibits a single wavelength absorption, then the copolymer will exhibit a single wavelength absorption and any color associated with a single wavelength absorption can be obtained. From PropOT-tBu$_2$ and PropOT-Me$_2$, copolymers generated from a gradient of monomer feed ratios were found to exhibit single wavelength spectra exhibiting all colors except green and black.

In the copolymer region, the mixture of PropOT-Me$_2$ and PropOT-tBu$_2$ consisting of a 1:1.5 wt % feed ratio generated the primary color red having a color coordinate of (0.420, 0.516). An electrochromic device was prepared in order to test the color accuracy of the diffusion-copolymerization approach of the high-throughput color screening method using the feed ratio of PropOT-Me$_2$ and PropOT-tBu$_2$ 1:1.5 wt %. The electrochromic device was fabricated using the in situ assembly approach as mentioned previously with the same gel electrolyte composition and adding 59.3 wt % of PropOT-tBu$_2$ and 40.7 wt % PropOT-Me$_2$. This device was then sandwiched between two ITO coated PET substrates. The PEG-DA was then cured using UV light at 320 μW/cm$^2$ intensity for 5 minutes. A potential of +3 V was applied to the device for 30 s, polymerizing the comonomers and the device was cycled between ±2 V. The color of the PPropOT-tBu$_2$-co-PPropOT-Me$_2$ displayed a red color in the neutral state and was transparent in the oxidized state, respectively, giving a color coordinate of u'=0.411 and v'=0.516 closely matching the color coordinate at the point for the selected respective feed ratio of u'=0.420 and v'=0.516 in the high-throughput screening device.

In System 2, 50% bithiophene and 2.5% EDOT were studied and the color coordinates u' and v' were measured to investigate the effect of the copolymer having different EDOT: bithiophene ratios. The copolymer region was closest to the EDOT reservoir as the saturation distance of EDOT is 3.3 mm. The copolymer region showed blue, purple and orange-purple.

TABLE 5

| Point between reservoirs* | Feed Ratio Bithiophene: EDOT | u' | v' |
|---|---|---|---|
| 1 | 1:0.09 | 0.160 | 0.365 |
| 2 | 1:0.05 | 0.221 | 0.434 |
| 3 | 1:0.02 | 0.251 | 0.479 |
|  | 100:0 | 0.275 | 0.530 |
|  | 0:100 | 0.164 | 0.320 |

*Distance between each point is about 1 mm.

To test the accuracy of the high throughput color selection process, a composition of bithiophene: EDOT was chosen as an example for the test measurement which had u'=0.25 and v'=0.47. Test devices were fabricated using the unmodified in situ assembly approach; the electrolyte gel was mixed with monomers between two electrodes. Then it was cured by using UV and was then converted. The color coordinate of the test device was u'=0.251 and v'=0.482. By comparing this value with the color coordinate of the aforementioned composition, the color coordinates of the two devices were substantially similar to each other. Not wishing to be bound by theory, but it is suggested that the slight offset between the two points is due to the different polymerization conditions; the monomer was mixed with the gel before assembly in the test devices, but the monomer had to diffuse into the solid-state gel matrix in the color selection platform, which could lead to different morphology of the polymer and affect the color outcome.

In System 3, the concentration of bithiophene was kept constant at 50% and the concentration of PropOT-Me$_2$ was changed. In the first device, the concentration of PropOT-Me$_2$ was 25%. The copolymer region was closest to the PropOT-Me$_2$ reservoir as the saturation distance of PropOT-Me$_2$ is 1.7 mm. The copolymer shows the colors blue, purple and pink. In the second device, purple and pink are observed in the copolymer region due to the decrease of the concentration of PropOT-Me$_2$ to 15%. The color coordinates for two points in the devices are shown in Table 6.

TABLE 6

| Point between reservoirs | Feed Ratio ProDOT-Me$_2$: Bithiophene | u' | v' |
|---|---|---|---|
| | System A | | |
| 1 | 0.7:1 | 0.237 | 0.2698 |
| 2 | 0.13:1 | 0.34 | 0.462 |
| | System B | | |
| 1 | 0.34:1 | 0.273 | 0.37 |
| 2 | 0.11:1 | 0.343 | 0.42 |
| | 0:100 | 0.275 | 0.530 |
| | 100:0 | 0.172 | 0.272 |

As shown by the three systems, the diffusional behavior of the individual monomers and the color coordinates allows for the monomer feed ratio to be determined for any given color.

Although the above are exemplified with copolymers of two monomers, the approach can be extended to three or more monomers.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including", and "containing" are to be construed as open-ended terms (i.e., meaning "including, but not limited to") unless otherwise noted. "Or" means and/or. Recitation of ranges of values herein are merely intended to serve as a shorthand method of referring individually to each separate value falling within the range, unless otherwise indicated herein, and each separate value is incorporated into the specification as if it were individually recited herein. All ranges disclosed herein are inclusive and combinable. The modifier "about" used in connection with a quantity is inclusive of the stated value and has the meaning dictated by the context (e.g., includes the degree of error associated with measurement of the particular quantity). The term "or" means "and/or."

Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The essential characteristics of the present invention are described completely in the foregoing disclosure. One skilled in the art can understand the invention and make various modifications without departing from the basic spirit of the invention, and without deviating from the scope and equivalents of the claims, which follow. Moreover, any combination of the above-described elements in all possible variations thereof is encompassed by the invention unless otherwise indicated herein or otherwise clearly contradicted by context.

What is claimed is:

1. A method for screening, comprises:
providing a screening device comprising at least two electrodes and a polymer electrolyte matrix disposed between the at least two electrodes, wherein the polymer electrolyte matrix comprises a plurality of reservoirs;
providing an electroactive monomer composition in the plurality of reservoirs, wherein the electroactive monomer composition comprises an electroactive monomer of a known concentration, a monomer composition solvent, and optionally a monomer composition salt, wherein each reservoir comprises a single electroactive monomer composition;
allowing the electroactive monomer of the electroactive monomer composition to diffuse through the polymer electrolyte matrix for a period of time;
polymerizing the electroactive monomer to form a composite of polymer electrolyte matrix and a conjugated polymer, or a composite of polymer electrolyte matrix and a conjugated copolymer where two or more different electroactive monomers have diffused into the same area of the polymer electrolyte matrix;
determining the diffusion behavior of the monomer in the monomer compositions;
obtaining a property of the conjugated polymer or conjugated copolymer; and
correlating the property of the conjugated copolymers with monomer feed ratios.

2. The method of claim 1, wherein the property is CIELuv color coordinates.

3. The method of claim 1, further comprising predicting the composition of electroactive monomers to achieve a select color for a conjugated copolymer based on the correlating step.

4. The method of claim 1, wherein the screening device comprises a potential source in electrical connection with the at least two electrodes.

5. The method of claim 1, wherein the at least two electrodes are indium-doped tin oxide (ITO) coated substrates.

6. The method of claim 1, wherein polymerizing the electroactive monomer is effected by applying a voltage to the device or by exposing the polymer electrolyte matrix to bromine vapor.

7. The method of claim 1, wherein the polymer electrolyte matrix is a crosslinked gel electrolyte composition.

8. The method of claim 7, wherein the crosslinked gel electrolyte is formed by crosslinking a gel electrolyte precursor.

9. The method of claim 1, wherein the polymer electrolyte matrix comprises a lithium, sodium, or potassium salt, or an ionic liquid.

10. The method of claim 1, wherein the monomer composition salt is the same salt as present in the polymer electrolyte matrix.

11. The method of claim 1, wherein the allowing the electroactive monomer of the electroactive monomer composition to diffuse through the polymer electrolyte matrix for a period of time is for 1, 2, 3, 4, 5, 6, 7, 8, 9, 10, 12, 14, 16, 18, 20, 22, or 24 hours.

12. The method of claim 1, wherein the electroactive monomer is thiophene, substituted thiophene, carbazole, 3,4-ethylenedioxythiophene, thieno[3,4-b]thiophene, substituted thieno[3,4-b]thiophene, dithieno[3,4-b:3',4'-d]thiophene, thieno[3,4-b]furan, substituted thieno[3,4-b]furan, bithiophene, substituted bithiophene, pyrrole, substituted pyrrole, acetylene, phenylene, substituted phenylene, naphthalene, substituted naphthalene, biphenyl and terphenyl and their substituted versions, phenylene vinylene (e.g., p-phenylene vinylene), substituted phenylene vinylene, aniline, substituted aniline, indole, substituted indole, or a combination thereof.
13. The method of claim 1, wherein the electroactive monomer is
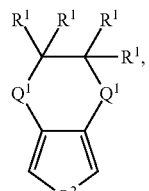 (I)
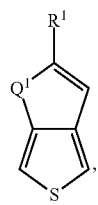 (II)
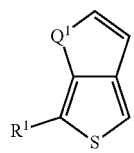 (III)
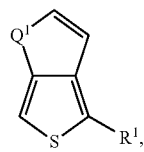 (IV)
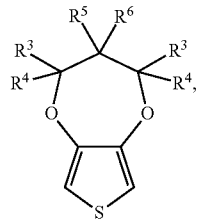 (V)
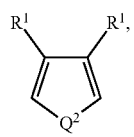 (VI)
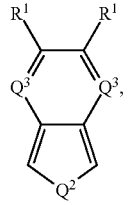 (VII)
 (VIII)
-continued
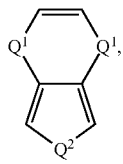 (IX)
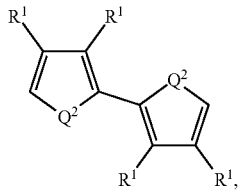 (X)
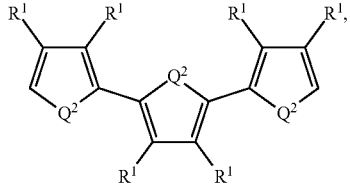 (XI)
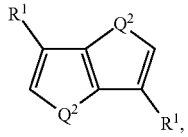 (XII)
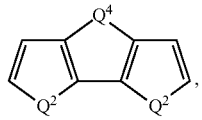 (XIII)
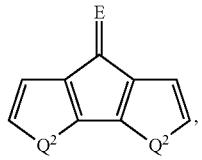 (XIV)
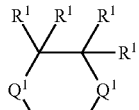 (XV)
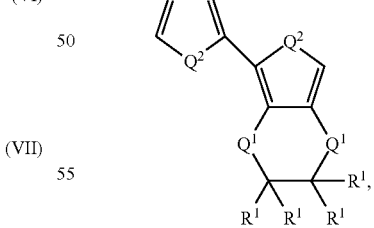 
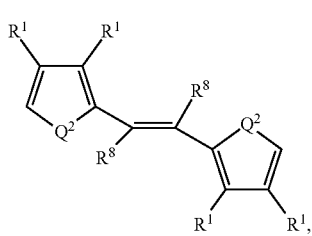 (XVI)

(XVII)
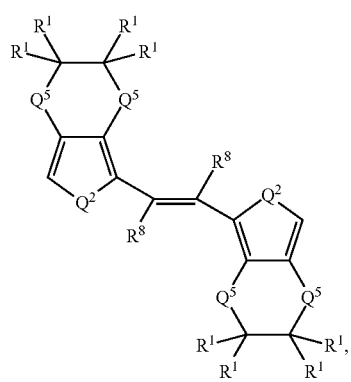
(XVIII)
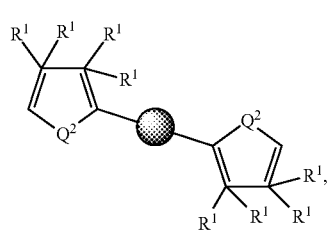
(XIX)
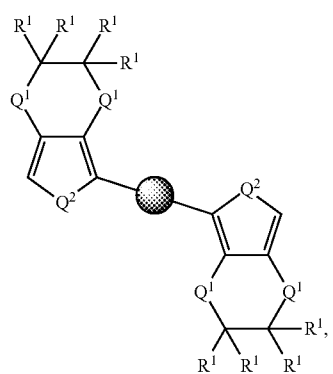
(XX)
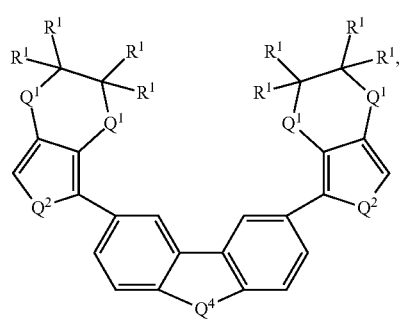
(XXI)
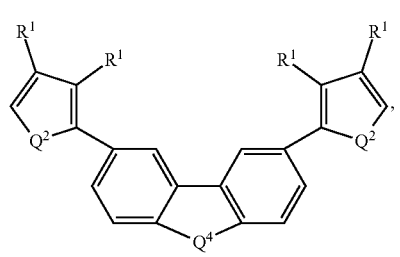
(XXII)
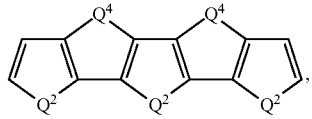
(XXIII)
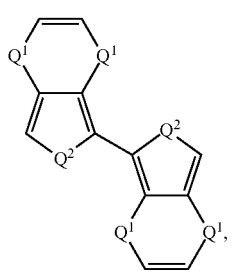
(XXIV)
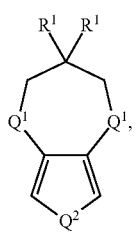
(XXV)
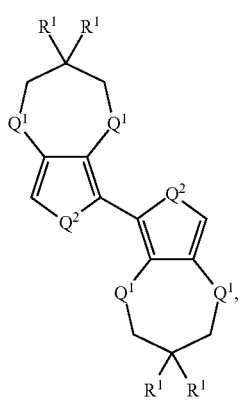
(XXVI)
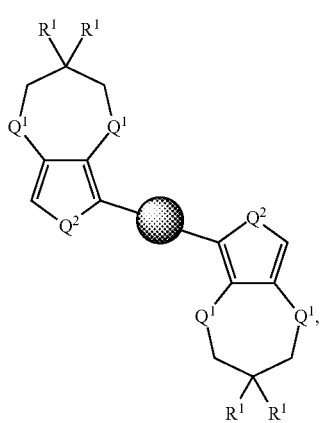

(XXVII)

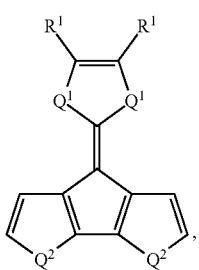

(XXVIII)

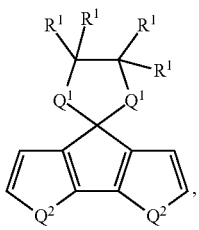

(XXIX)

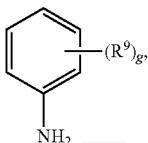

(XXX)

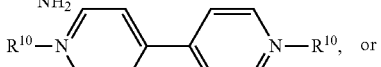

(XXXI)

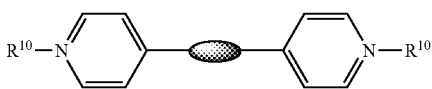

wherein
each occurrence of $Q^1$ is independently S, O, or Se;
$Q^2$ is S, O, or N—$R^2$;
each occurrence of $Q^3$ is independently CH or N;
$Q^4$ is $C(R^1)_2$, S, O, or N—$R^2$;
each occurrence of $Q^5$ is independently $CH_2$, S, or O;
each occurrence of $R^1$ is independently hydrogen, $C_1$-$C_{12}$ alkyl, $C_1$-$C_{12}$ alkyl-OH, $C_1$-$C_{12}$ haloalkyl, $C_1$-$C_{12}$ alkoxy, $C_1$-$C_{12}$ haloalkoxy, aryl, —$C_1$-$C_6$ alkyl-O-$C_1$-$C_6$ alkyl, or —$C_1$-$C_6$ alkyl-O-aryl;
$R^2$ is hydrogen or $C_1$-$C_6$ alkyl;
each occurrence of $R^3$, $R^4$, $R^5$, and $R^6$ independently is hydrogen; optionally substituted $C_1$-$C_{20}$ alkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$ alkyl-O-$C_1$-$C_{10}$ alkyl, —$C_1$-$C_{10}$ alkyl-O-aryl, —$C_1$-$C_{10}$ alkyl-aryl;
or hydroxyl;
each occurrence of $R^7$ is an electron withdrawing group;
each occurrence of $R^8$ is independently hydrogen, $C_1$-$C_6$ alkyl, or cyano;
each occurrence of $R^9$ is independently $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O-$C_1$-$C_6$ alkyl, —$C_1$-$C_6$ alkyl-O-aryl, or N—$R^2$;
each occurrence of $R^{10}$ is independently $C_1$-$C_{12}$ alkyl, $C_1$-$C_{12}$ haloalkyl, aryl, —$C_1$-$C_6$ alkyl-O-$C_1$-$C_6$ alkyl, or —$C_1$-$C_6$ alkyl-O-aryl;
E is O or $C(R^7)_2$;

represents an aryl;

is $C_2$, $C_4$, or $C_6$ alkenylene, an aryl or heteroaryl; and
g is 0, 1, 2, or 3.

* * * * *